United States Patent [19]

Paul et al.

[11] 4,255,597

[45] Mar. 10, 1981

[54] PROCESS FOR PREPARING HEXACHLOROCYCLOPENTADIENE

[75] Inventors: Kalidas Paul, Bolingbrook; Glendon D. Kyker, Glen Ellyn, both of Ill.

[73] Assignee: Velsicol Chemical Corporation, Chicago, Ill.

[21] Appl. No.: 141,458

[22] Filed: Apr. 18, 1980

Related U.S. Application Data

[63] Continuation-in-part of Ser. No. 77,463, Sep. 20, 1979.

[51] Int. Cl.³ .............................................. C07C 17/02
[52] U.S. Cl. .................................. 570/220; 570/226; 570/230; 570/231; 570/234; 570/253
[58] Field of Search ................................... 260/648 C

[56] References Cited

U.S. PATENT DOCUMENTS

| | | | |
|---|---|---|---|
| 2,945,893 | 7/1960 | Steinhofer et al. | 260/648 C |
| 3,073,869 | 1/1963 | Hanna et al. | 260/648 C |
| 3,624,169 | 11/1971 | Fruhwirth et al. | 260/654 H |

*Primary Examiner*—Delbert E. Gantz
*Assistant Examiner*—Joseph A. Boska

*Attorney, Agent, or Firm*—Dietmar H. Olesch; Robert J. Schwarz

[57] ABSTRACT

There is disclosed a process for the production of hexachlorocyclopentadiene comprising the steps of:

1. Reacting liquid cyclopentadiene and chlorine at a temperature of from about 0° to about 100° C. until an average of at least 4 chlorine atoms has been added per mole of cyclopentadiene to form a first-stage product;

2. heating the resultant liquid reaction product of Step 1 in a second stage at a temperature of from about 140° C. to below about 200° C. with chlorine in the presence of from about 0.0001% to about 5.0% (by weight) of an aromatic compound until the reaction products of Step 1 contain an average of about 6 chlorine atoms per molecule, based on cyclopentadiene starting material; wherein said aromatic compound contains from 1 to 3 aromatic rings; at least one of the rings containing a nitrogen atom;

3. vaporizing and heating the resulting reaction products of Step 2 in a third stage in the presence of chlorine to a temperature of above 450° C. until at least a major portion of said products are converted to hexachlorocyclopentadiene.

7 Claims, No Drawings

PROCESS FOR PREPARING HEXACHLOROCYCLOPENTADIENE

This application is a continuation-in-part of our copending application Ser. No. 77,463 filed Sept. 20, 1979.

FIELD OF THE INVENTION

An improved process for preparing hexachlorocyclopentadiene wherein a partially chlorinated cyclopentadiene is reacted with chlorine in the presence of an aromatic compound.

DESCRIPTION OF THE PRIOR ART

A process for the production of high purity hexachlorocyclopentadiene by the direct, non-catalytic reaction of liquid cyclopentadiene and chlorine is disclosed in U.S. Pat. No. 3,073,869. This process may be used to produce hexachlorocyclopentadiene in commercially practicable yields without the necessity of extensive purification procedures. In this process, liquid cyclopentadiene and chlorine are reacted in a first stage at a temperature of from about 0 to about 100 degrees centigrade until at least four chlorine atoms per mole of cyclopentadiene have been added, the resulting liquid reaction mixture is heated in a second stage at a temperature of from about 140 degrees centigrade to below 200 degrees centigrade with chlorine until the product from the first stage contains an average of about six chlorine atoms per mole of cyclopentadiene, and the reaction mixture is vaporized and heated in a third stage in the presence of chlorine to a temperature of above 450 degrees centigrade.

The third stage of the process of U.S. Pat. No. 3,073,869 is conducted in the vapor phase. In this stage solid products often form which plug up the vapor phase reactor; this coking eventually forces one to shut down the reaction until the vapor phase reactor can be unplugged.

Shutting down the process of U.S. Pat. No. 3,073,869 is to be avoided as much as possible; for it usually takes an inordinately long period of time to start it up again. Thus, for example, when this process is conducted on a commercial scale, it usually takes from about 8 to about 48 hours to start up the first stage reaction in the second-stage reactor.

It is an object of this invention to provide an improved process wherein coking in the vapor phase stage is minimized. It is a further object of this invention to provide an improved process wherein the time it takes to start up a dead reaction in the second-stage reactor is substantially reduced.

DETAILED DESCRIPTION OF THE INVENTION

In accordance with this invention, there is provided a process for the production of hexachlorocyclopentadiene comprising the steps of:

(a) reacting liquid cyclopentadiene and chlorine at a temperature of from about 0 to about 100 degrees centigrade until a minimum of four chlorine atoms has been added per mole of cyclopentadiene to form a first-stage product;

(b) heating the resultant liquid reaction product of step (a) in a second stage at a temperature of from about 140 degrees centigrade to below about 200 degrees centigrade with chlorine in the presence of from about 0.0001 percent to about 5.0 percent (by weight) of an aromatic compound until the reaction products of step (a) contain an average of about six chlorine atoms per molecule, based on cyclopentadiene starting material;

(c) vaporizing and heating the resulting reaction products of step (b) in a third stage in the presence of chlorine to a temperature of about 450 to about 600 degrees centigrade until at least a major portion of said products are converted to hexachlorocyclopentadiene; and (d) recovering therefrom hexachlorocyclopentadiene; wherein said aromatic compound has the structural formula selected from the group consisting of

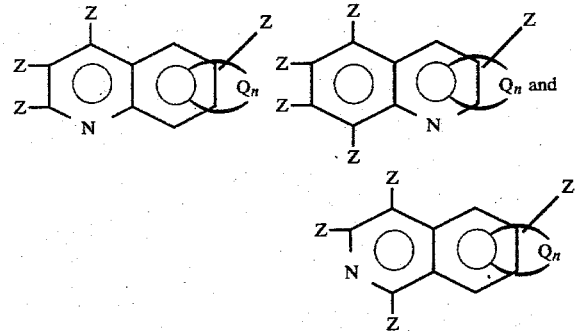

wherein n is 0 or 1; Q forms a sixmembered ring having 5 or 6 carbon atoms and 0 or 1 nitrogen atoms and attached to adjacent carbon atoms of the ring; each Z is independently selected from the group consisting of hydrogen, hydroxy, lower alkyl, lower alkoxy, nitro,

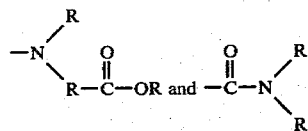

wherein each R is independently selected from the group consisting of hydrogen and lower alkyl.

The term lower as used herein designates a straight or branched carbon chain of 1 to 5 carbon atoms.

Applicants have discovered that, unexpectedly, the novel process of this invention allows them to obtain a product with higher proportions of the desired hexachloro- and heptachloro- derivatives, it reduces coking in the vapor phase chlorination step and the line blockage caused by it, and reduces the amount of start up time required for a dead reaction in the second-stage reactor.

The first stage of the present process involves reacting liquid cyclopentadiene and chlorine at relatively low temperatures so as to add a minimum of four chlorine atoms per mole of cyclopentadiene. Generally the temperature for this liquid phase reaction should be maintained between about 0° C. and about 100° C., it being preferred to perform this reaction at a temperature below about 60° C., with optimum practical results being obtained at reaction temperatures between about 20°-60° C.

During the first stage chlorination reaction, it is necessary that the reaction mixture be saturated with chlorine so as to substantially prevent the formation of polymer.

While the theoretically required amount of chlorine is 2 moles per mole of cyclopentadiene, it is desirable to use excess chlorine. The necessary excess varies with the reaction temperature, but generally cyclopentadiene:chlorine ratios between about 1:2 and 1:4 are sufficient, the exact concentration not being critical. Actually a chlorine excess of above 50% is not of consequential value.

Superatmospheric pressure is not required for this low temperature reaction, but since there is involved a gaseous reactant, a closed reaction vessel is employed for the first stage. The reaction time is relatively short, up to about 5 hours, and is dependent on the reaction temperature, pressure (if employed), concentration of reactants, type of equipment, and whether the process is conducted as a batch or continuous operation.

The resulting reaction mixture from the first stage low temperature chlorination reaction contains a mixture of compounds of the formula

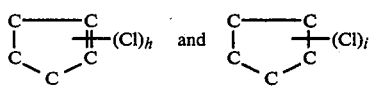

wherein h is from 1 to about 8 and i is about 4 to about 8; said reaction mixture contains from about 68 to about 72 percent (by weight) of chlorine. It is preferred that h be selected from the group consisting of 3, 4, 5, and 6 and that said reaction mixture contain about 70 percent (by weight) of chlorine.

The resulting reaction mixture from the first stage low temperature chlorination reaction is then further chlorinated in the liquid phase with chlorine in a second stage closed reaction vessel in the presence of the aromatic compound herein further described.

In this second stage reaction of the present process, the reaction temperature is of critical importance. The second stage reaction, in essence, is the reaction of the previously described first stage reaction product and chlorine at a temperature between about 140° C. and below 200° C., and preferably between about 150° C. and about 185° C., to produce a reaction product containing an average of 6 chlorine atoms per molecule of cyclopentadiene starting material. As in the case of the first stage chlorination, no catalyst need be employed. At temperatures above this critical area, as discussed previously, there is produced octachlorocyclopentene.

As in the first stage reaction, this second stage reaction is performed using atmospheric pressure, although superatmospheric pressures can be advantageous.

Theoretically, 2 moles of chlorine are required per mole of tetrachlorinated material. Tetrachlorinated reactants: chlorine ratios between about 1:2 and 1:6 are satisfactory. The presence of chlorine in amounts above this 200% excess is not of value.

While each of the various liquid phase chlorination reactions of the present process can be performed as a batch process, it is a preferred embodiment of the present process to use it as a continuous process. This is particularly so for the first two stages since they are both liquid phase chlorination reactions, the second using the product of the first as its starting material. In utilizing a continuous process for the first two reactions, the chlorine can be introduced countercurrent to the process stream, i.e., being introduced into the second stage reaction and then into the first stage reaction.

In the process of this invention, the liquid reaction mass from stage one of the process is heated at a temperature of from about 140° C. to below about 200° C. with chlorine in the presence of from about 0.001% to about 5.0% (by weight) of a preferred aromatic compound until the first stage reactant contains an average of about 6 chlorine atoms per mole of cyclopentadiene. It is preferred to use from about 0.0003 to about 1.0% (by weight of the liquid reaction mass from stage one) of said compound in this second stage, although it is more preferred to use from about 0.0005 to about 0.009% (by weight) of said aromatic compound; it is most preferred to sue from about 0.0006 to about 0.0008% (by weight) of said aromatic compound in the second stage of this process.

The aromatic compounds useful in the process of the present invention have the structural formula selected from the group consisting of

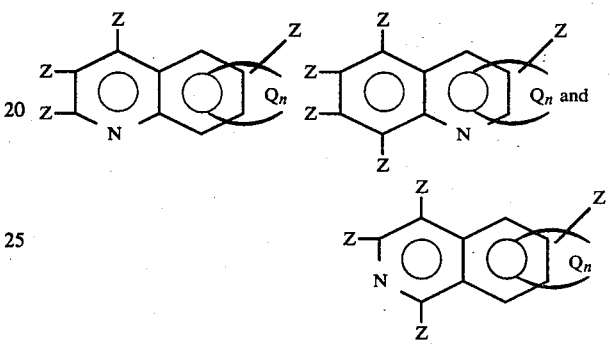

wherein n is 0 or 1; Q forms a sixmembered ring having 5 or 6 carbon atoms and 0 or 1 nitrogen atoms and attached to adjacent carbon atoms of the ring; each Z is independently selected from the group consisting of hydrogen, hydroxy, lower alkoxy, nitro,

wherein each R is independently selected from the group consisting of hydrogen and lower alkyl. It is preferred that a maximum of 2 of the Z substituents be substituents other than hydrogen.

The term lower as used herein designates a straight or branched carbon chain of 1 to 5 carbon atoms.

Exemplary compounds of the above-described formulas include phenanthroline, 3-hydroxyisoquinoline, 3-carboxyisoquinoline, 1,3-dicarboxyisoquinoline, 1,3-dihydroxyisoquinoline, 4,5-dihydroxy acridine, 4-carboxyacridine, 2-hydroxybenzoquinoline, 2-hydroxybenzoquinoline, 2,4-dihydroxybenz [f] isoquinoline, 8-hydroxyquinoline, 2-methoxyphenanthroline, 1,3-dicarbethoxylisoquinoline, 3-dipropylamidoisoquinoline, 1,3-dipentylaminoisoquinoline, 2,10-diethoxybenzo [g] quinoline, 10-carbethoxybenzo [g] quinoline, 2-hydroxybenzo [f] isoquinoline, 4-propyl-5-di(butyl)aminobenzo [f] isoquinoline, 2,4-dicarboxybenzo [f] isoquinoline, 2-ethoxy-4-carbethoxybenzo [f] isoquinoline, benzo [f] isoquinoline; 1-butyl-4-carboxycarbazole, 2-hydroxy acridine, 2,6-dicarboxy-4-ethyl acridine, 3-hydroxy-4-methyl acridine, 1,5-dimethylamino-3-hydroxy-acridine, 2,8-di(ethoxy carbonyl)acridine, 4,5-diacetoamidoacridine, 3-methyl-5-methoxy-7-nitropyrido [3,2-g] quinoline, 4,6-dicarboxypyrido [3,2-g] quinoline, 4,6-dicarboxypyrido [3,2-g] quinoline, 2-carbethoxy-pyrido [3,2-g] quinoline, 4-methoxy-7- methyl-10-carboxy-benzo [g] isoquinoline, 3-carbomethoxy-6-nitro benzo [g] isoquinoline, 4-(dipentylamido)-benzo [g] isoquinoline, 3-(methylethyl amino)-5-isopropy benzo [g] isoquinoline and the like.

As in the case of the liquid phase reactions, the vapor phase reaction is normally conducted on a continuous basis. Also, as in the case of the liquid reactions, no catalyst is required.

Thus, it can be seen that the present process utilizes three reactions or stages, two in the liquid phase and one in the vapor phase in producing substantially quantitative yields of good purity hexachlorocyclopentadiene, i.e. 90–98% assay. If even higher purity product is required, this can be readily accomplished by fractional distillation. By use of this method of purification hexachlorocyclopentadiene of 98% and higher assay is obtainable.

The following examples are provided for the purpose of further illustration only and are not intended to be limitative of the invention. Unless otherwise specified, all parts are by weight, all weights are in grams, all temperatures are in degrees centigrade, and all volumes are in milliliters.

EXAMPLE 1

Carbon tetrachloride was placed in a 5-necked glass reaction flask. Chlorine gas was added so as to saturate the carbon tetrachloride. The purpose of the carbon tetrachloride was to insure the presence of the necessary excess of chlorine and required dilution of cyclopentadiene. Cyclopentadiene was then continuously added to the reaction mixture while the chlorine gas was continuously incorporated. Throughout the reaction, the mixture was maintained at a temperature of 40 degrees centigrade. The desired tri and tetrachlorinated products were then freed from the carbon tetrachloride by distillation in the presence of excess chlorine. Additional chlorine was then injected, and the temperature was maintained at 170 degrees centigrade. Approximately quantitative yields of the desired hexachlorinated second-stage product were recovered; analysis indicated that it contained 75.7 percent of chlorine.

EXAMPLE 2

Cyclopentadiene is cooled to a temperature of about −20 degrees centigrade.

The cooled cyclopentadiene is continuously fed along with chlorine gas to a first-stage reactor. About 2 moles of chlorine per mole of cyclopentadiene are continuously fed to the first-stage reactor, and the reaction mixture is maintained at a temperature of about 45 degrees centigrade. The reaction is continued until a partially chlorinated product with a specific gravity of from about 1.50 to about 1.60 is obtained; this product is then fed to the second-stage reactor.

EXAMPLES 3 AND 4

In substantial accordance with the procedure of Example 2, chlorinated first-stage product was prepared. Portions of this first-stage product were converted to second-stage product by chargint them to a 4-neck 250 milliliter flask fitted with a stirrer, a thermometer, and a chlorine inlet and outlet; 250 grams of chlorinated first-stage reactant with a specific gravity of about 1.55 were used in each experiment.

In each of these examples, the reaction mixture was heated with a thermowatch-controlled heating mantle; heat was turned on, and chlorine was introduced into the flask at a rate of 0.08 pounds per hour until a reaction temperature of 334–341 degrees Fahrenheit was reached. The chlorine flow rate was maintained at 0.2 pounds per hour until a product with a specific gravity of 1.70 (at 35 degrees centigrade) was obtained.

Table 1 indicates the additive used and its concentration, the specific gravity of the chlorinated product produced, and the percentages of the product which was tri, tetra, penta, hexa and octachlorinated products.

TABLE 1

| Ex. # | Additive/ Conc. ppm | Sp.Gr. @ 35° C. | $Cl_3$ | $Cl_4$ | $Cl_5$ | $Cl_6$ | $Cl_7$ | $Cl_8$ |
|---|---|---|---|---|---|---|---|---|
| 3 | phenanthroline 19.5 | 1.699 | .71 | 6.6 | 6.6 | 39.0 | 40.2 | 6.6 |
| 4 | None | 1.7069 | 2.03 | 19.6 | 5.38 | 29.66 | 6.36 | 33.75 |

COMPARATIVE EXAMPLE 5

A partially chlorinated cyclopentadiene produced in substantial accordance with the procedure of Example 2 with a specific gravity of 1.54 was continuously fed to a reactor together with gaseous chlorine; no aromatic compound was introduced into the system. The reaction mixture was maintained at a temperature of 165°–180° C. The feed rates were adjusted to a chlorine/cyclopentadiene mole ratio of about 5.87; about 30 mole% of unreacted chlorine was present in the system. The reaction time was about 5.7 hours, and a chlorinated cyclopentadiene product with a specific gravity of about 1.675 was continuously removed from the reaction system. Heat had to be supplied to the reaction mixture in order to maintain the reaction temperature.

Once during this reaction the chlorine feed was inadvertently stopped for a period of about 4.0 hours; during this period, the reaction mixture was heated and maintained at a temperature of from 165°–180° C. The chlorine feed to the system was resumed, and an attempt was made to "start up" the reaction again. It required a period of nearly 24 hours before the reaction proceeded at a rate equivalent to the one obtained before the chlorine feed was disrupted; and even after this period of time, heat had to be supplied from an external heater to maintain the reaction temperature. The resulting product composition contained about 70% of the tri-, tetra- and octachlorocyclic compounds, while there were only about 30% of the penta-, hexa-, and heptachloro-products.

The above examples have been described roe the purpose of illustration and not limitation. Many other modifications will suggest themselves to those skilled in the art; they are intended to be comprehended within the scope of this invention.

The embodiments of this invention in which an exclusive right or privilege is claimed are as follows:

1. A process for the production of hexachlorocyclopentadiene comprising the steps of:
   (a) reacting liquid cyclopentadiene and chlorine at a temperature of from about 0° to about 100° C. until a minimum of 4 chlorine atoms has been added per mole of cyclopentadiene to form a first-stage product;
   (b) heating the resultant liquid reaction product of step (a) in a second stage at a temperature of from about 140° C. to below about 200° C. with chlorine in the presence of from about 0.001% to about 5.0% (by weight) of an aromatic compound until the reaction products of step (a) contain an average of about 6 chlorine atoms per molecule, based on cyclopentadiene starting material; wherein said aromatic compound is selected from the group consisting of phenanthroline and 8-hydroxy-quinoline (c) vaporizing and heating the resulting reaction products of step (b) in a third stage in the presence of chlorine to a temperature of above 450° C. until at least a major portion of said products are converted to hexachlorocyclopentadiene; and (d) recovering therefrom hexachlorocyclopentadiene.

2. The process of claim 1, wherein liquid cyclopentadiene and chlorine are reacted in a first stage at a temperature of from about 20° to about 60° C. until at least 4 chlorine atoms have been added per mole of cyclopentadiene.

3. The process of claim 2, wherein the resultant liquid reaction mixture is heated in a second stage at a temperature of from about 150° to about 185° C. in the presence of from about 0.0005 to about 0.009% (by weight of said liquid reaction mixture) of said aromatic compound to produce a reaction product containing an average of 6 chlorine atoms per mole of cyclopentadiene.

4. The process of claim 3, wherein from about 2 to about 6 moles of chlorine per mole of tetrachlorinated material in said resultant liquid reaction mixture are heated in a second stage at a temperature of from about 150 to about 185° C.

5. The process of claim 4, wherein from about 0.0006 to about 0.0008% (by weight) of said aromatic compound is heated with resultant liquid reaction mixture and chlorine in the second stage.

6. The process of claim 1, wherein said aromatic compound is phenanthroline.

7. The process of claim 1, wherein said aromatic compound is 8-hydroxyquinoline.

* * * * *